(12) United States Patent
Naser et al.

(10) Patent No.: US 6,290,943 B1
(45) Date of Patent: *Sep. 18, 2001

(54) STABLE MULTIPLE EMULSION COMPOSITION

(75) Inventors: Mark Stephen Naser, Hamburg, NJ (US); Tirucherai Vasudevan, Lake Zurich, IL (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/425,366

(22) Filed: Oct. 22, 1999

(51) Int. Cl.[7] ............................. A61K 7/06; A61K 7/08; A61K 7/00

(52) U.S. Cl. ................. 424/70.15; 424/70.1; 424/70.11; 424/70.21; 424/70.19; 424/70.22; 424/70.31; 424/401

(58) Field of Search ................................. 424/401, 70.1, 424/70.11, 70.15, 70.21, 70.22, 70.31, 70.19

(56) References Cited

U.S. PATENT DOCUMENTS

| | | |
|---|---|---|
| 4,254,105 | 3/1981 | Fukuda . |
| 5,306,498 | 4/1994 | Vesperini et al. . |
| 5,332,595 | 7/1994 | Gaonkar . |
| 5,567,426 | 10/1996 | Nadaud et al. . |
| 5,589,177 | 12/1996 | Herb et al. . |
| 5,656,263 | 8/1997 | Fructus . |
| 5,656,280 | 8/1997 | Herb et al. . |
| 5,948,855 | * 9/1999 | Lin et al. . |
| 6,103,267 | * 8/2000 | Mitchnick et al. . |

FOREIGN PATENT DOCUMENTS

| | | |
|---|---|---|
| 0715842 | 6/1996 | (EP) . |
| 0717978 | 6/1996 | (EP) . |
| 0908170 | 4/1999 | (EP) . |

OTHER PUBLICATIONS

International Search Report Application No. PCT/EP 00/10378 mailed Feb. 23, 2001.

* cited by examiner

Primary Examiner—Thurman K. Page
Assistant Examiner—Brian K. Seidleck
(74) Attorney, Agent, or Firm—Ronald A. Koatz

(57) ABSTRACT

$W_1$-O-$W_2$ emulsions are disclosed in which the $W_1$/O emulsion comprises an internal aqueous phase containing a benefit agent and an oil phase surrounding it, and, around this is found an external isotropic aqueous phase. It is critical that the external surfactant phase not comprise an amido containing anionic. It is also critical that oil be not greater than 50% unsaturated and not be a volatile silicone.

16 Claims, 1 Drawing Sheet

A stable multiple emulsion where a water droplet (W1) surrounded by oil maintains its integrity in a concentrated isotropic surfactant phase (W2)

An unstable (broken) multiple emulsion becomes a "simple" emulsion where oil droplets are surrounded by a mixed W1/W2 phase ((O/(W1+W2))

A stable multiple emulsion where a water droplet (W1) surrounded by oil maintains its integrity in a concentrated isotropic surfactant phase (W2)

Figure 1B

An unstable (broken) multiple emulsion becomes a "simple" emulsion where oil droplets are surrounded by a mixed W1/W2 phase ((O/(W1+W2))

STABLE MULTIPLE EMULSION COMPOSITION

FIELD OF THE INVENTION

The present invention relates to liquid surfactant composition, e.g., liquid shower gels or liquid shampoos, comprising multiple emulsions. In particular, this invention relates to such compositions which may comprise high levels of surfactants while the multiple emulsion is nonetheless stable.

BACKGROUND OF THE INVENTION

Multiple emulsion systems (broadly defined as systems in which water/oil and oil/water emulsion co-exist) are very valuable because these permit incorporation and enhanced delivery of benefit agents. Thus, these multiple emulsions have been used for many years, for example, in cosmetic and pharmaceutical areas to deliver cosmetic or pharmacological benefit agents (see for Example, U.S. Pat. No. 5,306,498 to Vesperini; or U.S. Pat. No. 5,567,426 to Nadaud et al.).

In general, however, as the level of cleansing surfactant (e.g., having high HLB, e.g., HLB greater than 10, preferably greater than 12) in such multiple emulsion systems is increased, the emulsions become less and less stable. Thus, for example, the level of cleansing surfactant in almost all the cosmetic and pharmaceutical art referred to above is below 5% by wt. of the compositions.

In U.S. Pat. No. 5,656,280 to Herb et al., and U.S. Pat. No. 5,589,177 to Herb et al. as well as in equivalent EP 717,978 and EP 715,842, both assigned to Helene Curtis, there is disclosed the stabilization of multiple emulsions in compositions containing high levels of conditioning surfactant. In these references, however, the stable multiple emulsion composition comprises surfactants (i.e., the conditioning surfactants of that invention) which must form stabilizing liquid crystals, i.e., lamellar liquid crystals. Those compositions described in the Herb patent where the surfactants formed an isotropic phase (for example, Example 29 at column 29 of U.S. Pat. No. 5,589,177 at lines 30–44) were unstable (see column 34, where stability of Example 29 is only 5 minutes). By contrast, the surfactant phase of the present invention is an isotropic surfactant phase, yet the multiple emulsion does not break into a simple emulsion when evaluated at room temperature for at least 2 weeks, preferably greater than 4 weeks, more preferably greater than 8 weeks, when measured at a temperature of about 25° C.

Compositions comprising isotropic surfactant phases are advantageous over compositions comprising lamellar liquid crystal phase at least because (1) they can be formed using a much wider range of surfactant; and (2) they provide improved foam/lather.

Accordingly, it is an object of the invention to provide a surfactant phase which is not constrained in that it has to be lamellar phase.

It is another object of the invention to provide a surfactant phase (which is an isotropic phase) which contains high levels of surfactant and yet does not destabilize the multiple emulsion.

BRIEF SUMMARY OF THE INVENTION

Unexpectedly, applicants have now found that it is possible to obtain multiple emulsion systems which comprise high levels of surfactant forming an isotropic phase and whereby the multiple emulsion can deliver desirable benefit agent (e.g., in the internal oil phase) while simultaneously maintaining the stability of the multiple emulsion. In previous art it has been difficult or impossible to make stable multiple emulsions in the presence of high levels of surfactant which form an isotropic phase. In preferred embodiments, the surfactant system comprises mixtures of anionic and amphoteric surfactants and levels of surfactant are greater than about 10.5% of total composition.

The invention further relates to methods of stabilizing these multiple emulsion systems described above.

More specifically, the invention comprises a water-in-oil-in-water ($W_1$-O-$W_2$) multiple emulsion wherein the water-in-oil ($W_1$/O) emulsion itself comprises an internal aqueous phase ($W_1$) which contains a solute and optional surfactant; an oil phase O (an oil combined with a low HLB emulsifier, e.g., emulsifier with HLB less than 10) surrounding the internal aqueous phase; and a topically active compound which may be in either the aqueous $W_1$ or in O. The $W_1$O phase is surrounded by an external aqueous isotropic phase ($W_2$) containing cleansing surfactant, optional topically active compound (which may be the same or different as the first optional topically active compound), and optional solute. (It should be understood that some solute will almost always be present in the surfactant or will be formed when adjusting pH). One criticality of the invention is that surfactant phase $W_2$ must not contain an anionic surfactant with an amido group.

A second criticality is that the oil in the O phase (1) should not be comprised of more than 50% unsaturated compounds; or (2) should not be a volatile silicone (e.g., a silicone having viscosity of 10 centistokes or less).

As noted above, the invention can be distinguished from prior art U.S. Pat. No. 5,656,280 for example in that that patent requires the aqueous phase $W_2$ (e.g., external aqueous phase) to comprise a surfactant system capable of forming stabilizing liquid crystals. By contrast, the present invention requires that the external aqueous phase be an isotropic phase. The isotropic phase in turn is formed by selection of a specific surfactant system which must not contain an anionic surfactant with an amido group.

By definition, lamellar phase is a liquid crystalline phase whereas an isotropic phase is micellar; optically a lamellar phase would show birefringence under a polarized light source while a micellar phase does not exhibit this feature.

In particular, the invention comprises a $W_1$-O-$W_2$ multiple emulsion composition comprising:

(1) about 1% to 99% by wt. of the composition, preferably 2% to 90% by wt., more preferably 5% to 80% of a $W_1$/O emulsion comprising;
   (a) about 1% to 99% of said emulsion of an internal aqueous phase comprising (i) water; (ii) 0.01 to 30% solute; and (iii) 0 to 30% surfactant;
   (b) about 0.1% to about 99%, preferably 0.5 to 95%, more preferably 1 to 80% of the emulsion of an oil phase surrounding said internal aqueous phase comprising a non-volatile silicone compound, a volatile hydrocarbon compound, a non-volatile hydrocarbon compound or a mixture thereof;
   (c) about 0.1 to 20%, preferably 1 to 15%, more preferably 1.5 to 15% of a low HLB emulsifier (e.g., having HLB under 10); and
   (d) a topically effective amount (e.g., 0.01 to 40%, preferably 0.05 to 15% by wt.) of a first topically active compound which may be found in either aqueous phase (a) and/or oil phase (b); and (2) about 1 to 99% by wt., preferably 20 to 95% by wt. of an external isotropic aqueous phase $W_2$ comprising non-amido anionic and/or other surfactants. Preferably the composition contains anionic and amphoteric surfactants, wherein the ratio of first surfactant (preferably anionic) to amphoteric is 100:1 to 1:100. The composition optionally contains a second topically effective compound, typically 0–40% by wt. of the external phase to perform a function identical to, similar to or different from the first topically active compound, and solute. The surfactant typically will comprise 2–80% of the aqueous phase.

The $W_1$-O-$W_2$ multiple emulsion compositions are stable (e.g., typically they will not break down into a simple emulsion at room temperature for at least two weeks) and they exhibit exceptional esthetic and functional properties. The $W_1$-O-$W_2$ multiple emulsion compositions are liquids or creams, and are capable of effectively delivering one or more topically active compounds to the skin or hair from a single composition.

BRIEF DESCRIPTION OF THE DRAWING FIGURES

FIG. 1 is a schematic drawing wherein FIG. 1A shows a stable multiple emulsion in which the $W_1$/O phase is surrounded by the $W_2$ phase and FIG. 1B shows a multiple emulsion which has broken down into a simple O/($W_1$+$W_2$) emulsion.

DETAILED DESCRIPTION OF THE INVENTION

The present invention relates to $W_1$-O-$W_2$ multiple emulsion compositions comprising:

(1) 1 to 99% $W_1$/O emulsion comprising about 1% to 99% of $W_1$ (containing water, solute and optional surfactant), and 0.5 to 99% of O phase (containing oil compound and low HLB emulsifier). A topically active agent may be present in $W_1$ phase, O phase or both; and (2) about 1% to 99% by wt. of an external aqueous phase comprising non-amido anionic and/or other surfactants. The phase preferably comprises anionic, amphoteric, optional second topically effective compound, and solute.

Figures 1, 1A:
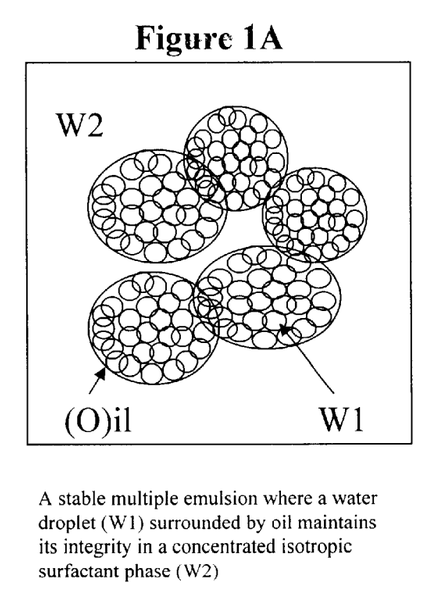
Figures 1, 1B:
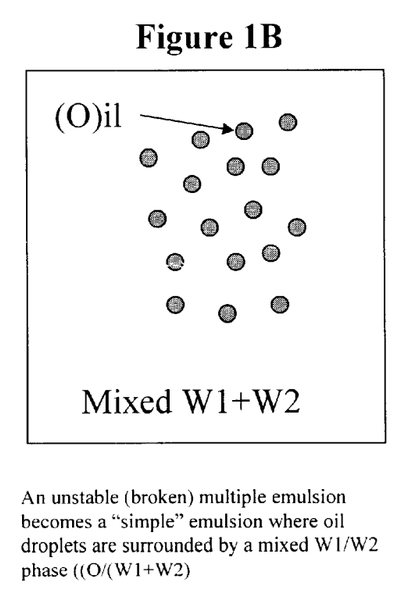

The external aqueous phase W2 (1 to 99% of total emulsion) differs from the art in that it is an isotropic, aqueous surfactant phase rather than a lamellar phase. These compositions are able to comprise relatively large amounts of surfactants (i.e., 10.5% by wt. or greater, preferably 11%–75%, more preferably 12% to 60%, more preferably 13% to 60%, more preferably 15% to 60%, more preferably 16% to 55%, more preferably 17 to 50% by wt. of the composition) while the integrity of the multiple emulsion still remains. Unless the surfactant system and oil are specifically selected as described herein, such multiple emulsion compositions will generally break very rapidly into simple emulsion (see FIG. 1).

The invention will now be described in greater detail.

The Water-in-Oil ($W_1$/O) Emulsion

The $W_1$/O emulsion comprises an internal aqueous phase $W_1$ with water, solute and optional surfactant, and an oil phase O.

Generally the water, solute and first topically-active compound comprise the internal aqueous phase of the $W_1$/O emulsion (active compound may also be in oil phase if oil compatible). That is, the $W_1$ phase comprises droplets containing water, solute and possibly a first topically-active compound. For example, droplets containing water, solute and a first topically-active compound ($W_1$) may have a diameter ranging from about 0.01 to about 75$\mu$ and may be enveloped by a membrane or film comprising the oil phase. The contents of the internal aqueous phase ($W_1$) therefore do not contact the external aqueous phase ($W_2$) of the $W_1$-O-$W_2$ multiple emulsion.

The primary $W_1$/O emulsion is present in a $W_1$-O-$W_2$ multiple emulsion composition in an amount of about 1% to about 99%, preferably 2% to 90%, more preferably about 5% to about 80%, by weight of the multiple emulsion composition. To achieve the full advantage of the present invention, the primary $W_1$/O emulsion is present in an amount of about 10% to about 80% by weight of the multiple emulsion composition.

The Internal Aqueous Phase

The (W1) internal aqueous phase constitutes about 1% to about 99% by weight of the emulsion, an oil phase separates the internal aqueous phase ($W_1$) of the emulsion from the external aqueous phase ($W_2$).

The internal aqueous phase ($W_1$) of the present $W_1$-O-$W_2$ multiple emulsion compositions generally comprise water, solute and an optional first topically-active compound (which may also be found in oil phase alone or in both). The internal aqueous phase can further comprise additional topically-active compounds and/or optional water soluble compounds capable of providing a desired esthetic or functional effect, such as a fragrance.

The aqueous phase ($W_1$) comprises about 1% to about 99%, and preferably about 10% to about 95%, by weight of the $W_1$/O emulsion. To achieve the full advantage of the present invention, the aqueous phase comprises about 25% to about 95% by weight of the $W_1$/O emulsion.

Topically-Active Compounds

In accordance with an important feature of the present invention, a wide variety of topically active compounds can be incorporated into the $W_1$/O emulsion as the first topically active compound. If found in the $W_1$ phase, the topically active compounds are water soluble or water dispersible and include both cosmetic and other compounds that act upon contact with the skin or hair. The first topically active compound is present in a sufficient amount to perform its intended function, typically in an amount of about 0.01% to about 40% by weight, preferably 0.05 to 15% of the $W_1$O emulsion.

The first topically active compound typically remains on the skin or hair after application, as opposed to being rinsed from the skin or hair. However, particular first topically active compounds are designed to be rinsed from the skin or hair after the compound performs its intended function.

In accordance with an important feature of the present invention, the first topically active compound can be incorporated into the aqueous phase or into the oil phase of the primary emulsion. Whether a particular first topically active compound is incorporated into the aqueous phase or the oil phase of the primary emulsion is related to the solubility of the topically active composition in water. In preferred embodiments, the first topically active compound is water soluble and is incorporated into the internal $W_1$ aqueous phase. However, a more hydrophobic agent may be used in the oil phase.

As used herein, the term "water soluble" means water soluble or water dispersible. A water soluble compound has a water solubility of at least 0.1 g (grams) per 100 ml (milliliters) of water and forms a true solution. A water soluble compound can be inherently water soluble or can be made water soluble by the addition of a solubilizing compound, such as a coupling agent, a co-surfactant, or a solvent. A water dispersible compound remains dispersed in water for at least the time period necessary to manufacture the primary $W_1/O$ emulsion, i.e., at least about one hour.

In addition, the topically active compound can be incorporated into the external aqueous phase $W_2$ to achieve enhanced efficacy.

The topically active compound therefore can be one of, or a combination of, a cosmetic compound, a medicinally active compound or any other compound that is useful upon topical application to the skin or hair. Such topically active compounds include, but are not limited to, hair and skin conditioners, hair and skin cleansers, hair fixatives, hair dyes, hair growth promoters, deodorants, skin care compounds, permanent wave compounds, hair relaxers, hair straighteners, antibacterial compounds, antifungal compounds, anti-inflammatory compounds, topical anesthetics, sunscreens and other cosmetic and medicinal topically effective compounds.

In accordance with one aspect of the present invention, the topically active compound comprises a water soluble hair conditioner, such as a quaternary ammonium compound. Quaternary ammonium compounds are substantive to the hair and are excellent hair conditioners, but have a well known incompatibility with anionic surfactants and anionic dyes. Therefore, quaternary ammonium compounds generally are not a component in shampoo conditioner compositions or anionic dye-based compositions, but are applied to the hair from a separate conditioning composition.

The water soluble quaternary ammonium compounds have the general structural formula:

wherein $R_1$ is an alkyl group including from about 8 to about 18 carbon atoms; $R_2$ is selected from the group consisting of an alkyl group including from about 8 to about 18 carbon atoms, a hydrogen atom, a methyl group, an ethyl group, a hydroxymethyl group and a hydroxyethyl group; $R_3$ is selected from the group consisting of a benzyl group, a hydrogen atom, a methyl group, a methyl group, a hydroxymethyl group and a hydroxyethyl group; $R_4$ is selected from the group consisting of a hydrogen atom, a methyl group, an ethyl group, a hydroxymethyl group and a hydroxyethyl group; and X is an anion. The quaternary nitrogen of the water soluble quaternary ammonium compound also can be a component of a heterocyclic nitrogen containing moiety, such as morpholine or pyridine. The anion of the quaternary ammonium compound can be any common anion, such as chloride, methosulfate, ethosulfate, nitrate, bromide tosylate, acetate, or phosphate.

The water soluble quaternary ammonium compounds have one or two long chain alkyl groups containing from about 8 to about 18 carbon atoms. The long chain alkyl groups also can include, in addition to, or in replacement of, carbon and hydrogen atoms, either linkages or similar water solubilizing linkages. The remaining two or three substituents of the quaternary nitrogen of the quaternary ammonium compound can be hydrogen; or benzyl, or short chain alkyl or hydroxyalkyl groups, such as methyl, ethyl, hydroxymethyl or hydroxyethyl groups; or combinations thereof, either of the same or different identity.

Exemplary water soluble quaternary ammonium compounds include, but are not limited to lautrimonium chloride; Quaternium-16; lauralkonium chloride; olealkonium chloride; dilauryidimonium chloride; cetalkonium chloride; dicetyldimonium chloride; laurylpyridinium chloride; cetylpyridinium chloride; soyatrimonium chloride; Polyquaternium-6; Polyquaternium-7; guarhydroxypropyltrimonium chloride; Polyquaternium-1 1; Polyquatemium-5; Polyquaternium-10; Polyquaternium-24; cetrimonium chloride; Quaternium-24; mytrimonium chloride; PEG-2 cocomonium chloride; PEG-2 cocoyl quaternium4; PEG-15 cocoyl quaternium-4; PEG-2 stearyl quaternium-4; PEG-2 oleyl quaternium-4; and PEG 15 olelyl quaternium-4, and mixtures thereof, wherein the compound designation is provided by the Cosmetic, Toiletry and Fragrance Association, Inc. in the *CTFA Cosmetic ingredient Dictionary*, 4th Ed., 1991, hereinafter referred to as the *CTFA Dictionary*. Other water soluble quaternary ammonium compounds are listed in the *CTFA Cosmetic Ingredient Handbook*, 1st Ed., 1988 (hereinafter the *CTFA Handbook*) at pages 40–42, incorporated herein by reference.

Other water soluble hair conditioners also can be used as the first topically active compound. Such hair conditioners include, but are not limited to, fatty amine salts, ethoxylated fatty amine salts, dimethicone copolyols, protonated polyethylenimines, protonated ethoxylated polyethylenimines, soluble animal collagen, lauramine oxide, cationic polymers, numerous other water soluble hair conditioners listed in the *CTFA Handbook* at page 71–73, incorporated herein by reference, and mixtures thereof.

In addition to hair conditioners, a skin conditioner can be used as the first topically active compound. Skin conditioning agents include, but are not limited to, humectants, such as fructose, glucose, glycerin, propylene glycol, glycereth-26, mannitol and urea; pyrrolidone carboxylic acid; hydrolyzed lecithin; coco-betaine; cysteing hydrochloride; glutamine; PPG-15; sodium gluconate; potassium aspartate; olelyl betaine, thiamine hydroxychloride; sodium laureth sulfate; sodium hyaluronate; hydrolyzed proteins; hydrolyzed keratin; amino acids; amine oxides; water soluble derivatives of vitamins A, E and D; amino functional silicones; ethoxylated glycerin; alpha-hydroxy acids and salts thereof; water soluble fatty oil derivatives, such as PEG-24 hydrogenated lanolin, almond oil, grape seed oil and castor oil; numerous other water soluble skin conditioners listed in the *CTFA Handbook*, pages 79–84, incorporated herein by reference; and mixtures thereof. Other conditioners include alpha hydroxy acids such as lactic acid, glycolic acid or their salts thereof.

The first topically active compound also can be a hair fixative or film former that imparts style retention properties to hair, i.e., sets the hair. The hair fixative typically is a homopolymer, a copolymer, or a terpolymer. The polymers can be nonionic, amphoteric, anionic or cationic. Examples of hair fixatives include, but are not limited to, an acrylamide copolymer; an acrylamide/sodium acrylate copolymer; a polystyrene sulfonate; a polyethylene oxide; a water dispersible polyester; a cationic cellulose; an acrylate/ammoniummethacrylate copolymer; an aminoethylacrylate phosphate/acrylate copolymer; a polyacrylamide; Polyquaternium-1; Polyquaternium-2; Polyquaternium-4; Polyquaternium-4; Polyquaternium-5; Polyquaternium-7;

Polyquaternium-8; Polyquaternium-9; Polyquaternium-10; Polyquaternium-11; Polyquaternium-12; Polyquaternium-13; Polyquaternium-14; Polyquaternium-15; Polyquaternium-16; Polyquaternium-28; a PVP (polyvinylpyrrolidone); a PVP/dimethylaminoethylmethacrylate copolymer; a PVP/ethyl methacrylate/methacrylic acid copolymer; a carboxylated polyvinyl acetate; vinyl/caprolactam/PVP/dimethylaminoethyl methacrylate copolymer (GAFFIX VC713); a PVP/vinyl acetate copolymer; a sodium acrylate/vinyl alcohol copolymer; sodium carrageenan; a vinyl acetate/crotonic acid copolymer; numerous other water soluble hair fixatives listed in the *CTFA Handbook* at pages 73–74, incorporated herein by reference; and mixtures thereof. Numerous hair fixatives also are disclosed in U.S. Pat. No. 5,277,899, incorporated herein by reference.

In addition, the first topically active compound can be a water soluble hair dye, such as, but not limited to, m-aminophenol hydrochloride, p-aminophenol sulfate, 2,3-diaminophenol hydrochloride, 1,5-naphthalenediol, phenylenediamine hydrochloride, sodium picramate, water soluble cationic dyes, water soluble anionic dyes, water soluble FD&C dyes, like Blue No. 1, Blue No. 2, Red No. 3, Red No. 4, or Red No. 40, water soluble D&C dyes, like Yellow No. 10, Red No. 22 or Red No. 28, and pyrogallol. Numerous other hair dyes are listed in the *CTFA Handbook*, pages 70–71, incorporated herein by reference.

The first topically active compound also can be an antioxidant, like ascorbic acid or erythorbic acid; or a fluorescent whitening agent or optical brightener, like a distyrylbiphenyl derivative, stilbene or a stilbene derivative, a pyralozine derivative or a coumarin derivative. In addition, a self-tanning compound, like dihydroxy acetone, or a hair growth promoter, or a hair bleaching agent, like a perborate or a persulfate salt, can be the first topically active compound.

The first topically active compound also can be a deodorant compound, such as an astringent salt or a bioactive compound. The astringent salts include organic and inorganic salts of aluminum, zirconium, zinc, and mixtures thereof. The anion of the astringent salt can be, for example, sulfate, chloride, chlorohydroxide, alum, formate, lactate, benzyl sulfonate orphenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides having the general formula $Al_2(OH)_xQ_y \cdot XH_2O$, wherein Q is chlorine, bromine or iodine; x is about 2 to about 5; x+y is about 6, wherein x and y are not necessarily integers; and X is about 1 to about 6. Exemplary zirconium compounds include zirconium oxy salts and zirconium hydroxy salts, also referred to as zirconyl salts and zirconyl hydroxy salts, and represented by the general empirical formula $ZrO(OH)_{2-nz}L_z$, wherein z varies from about 0.9 to about 2 and is not necessarily an integer; n is the valence of L; 2–nz is greater than or equal to 0; and L is selected from the group consisting of halides, nitrate, sulfamate, sulfate, and mixtures thereof.

Exemplary deodorant compounds therefore include, but are not limited to, aluminum bromohydrate, potassium alum, sodium aluminum chlorhydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, numerous other useful antiperspirant compounds listed in the *CTFA Handbook* at p. 56, incorporated herein by reference, and mixtures thereof.

In addition to the astringent salts, the deodorant compound can be a bacteriostatic quaternary ammonium compound, such as, for example, cetyl trimethyl ammonium bromide, cetyl pyridinium chloride, benzethonium chloride, diisobutylbenzoxyethoxyethyl-dimethylbenzyl ammonium chloride, sodium N-lauryl sarcosine, sodium N-polymethyl sarcosine, lauroyl sarcosine, N-myristolyl glycine, potassium N-lauroyl sarcosine, and stearyl trimethyl ammonium chloride; or a bioactive compound; or a carbonate or bicarbonate salt, such as, for example, the alkali metal carbonates and bicarbonates, and the ammonium and tetraalkylammonium carbonates and bicarbonates.

In addition, other compounds can be included in the primary emulsion as the first topically active compound in an amount sufficient to perform their intended function. For example, if the composition is intended to be a sunscreen then compounds such as benzophenone-4, trihydroxycinnamic acid and salts, tannic acid, uric acid, quinine salts dihydroxy naphtholic acid; an anthranilate, diethanolamine methoxycinnamate, p-aminobenzoic acid, phenylbenzimidazole sulfonic acid, PEG-25 p-aminobenzoic acid or triethanolamine salicylate can be incorporated into the internal aqueous $W_1$ phase.

Further, sunscreen compounds such as dioxybenzone, ethyl 4-[bis(hydroxypropyl)] aminobenzoate, glyceryl aminobenzoate, homosalate, menthyl anthranilate, octocrylene, octyl methoxycinnamate, octyl salicylate, oxybenzone, padimate O, red petrolatum, titanium dioxide, 4-menthylbenzylidene camphor, benzophenone-1, benzophenone-2, benzophenone-7, benzophenone-12, isopropyl dibenzoyl methane, butyl methoxydibenzoylmethane, zotocrylene, or zinc oxide can be incorporated into the oil phase of the primary emulsion. Other sunscreen compounds soluble in either the aqueous or organic phase are listed in *CTFA Handbook*, pages 87 and 87, incorporated herein by reference.

Similarly, topically active drugs, like antifungal compounds, antibacterial compounds; anti-inflammatory compounds; topical anesthetics; skin rash, skin disease and dermatitis medications; and anti-itch and irritation reducing compounds can be included in the compositions of the present invention. For example, analgesics such as benzocaine, dyclonine hydrochloride, aloe vera and the like; anesthetics such as butamben picrate, lidocaine hydrochloride, xylocaine and the like; antibacterials and antiseptics, such as povidone-iodine, polymyxin sulfate-bacitracin, zinc-neomycin sulfate-hydrocortisone, chloramphenicol, methylbenzethonium chloride, and erythromycin and the like; antiparastitics, such as lindane; deodorants, such as chlorophyllin copper complex, aluminum chloride, aluminum chloride hexahydrate, and methylbenzethonium chloride; essentially all dermatologicals, like acne preparations, such as benzoyl peroxide, erythromycin-benzoyl peroxide, clindamycin phosphate, 5,7-dichloro-8-hydroxyquinoline, and the like; anti-inflammatory agents, such as alcometasone dipropionate, betamethasone velerate, and the like; burn relief ointments, such as o-amine-p-toluene sulfonamide monoacetate and the like; depigmenting agents, such as monobenzone; dermatitis relief agents, such as the active steroid acinonide, diflorasone diacetate, hydrocortisone, and the like; diaper rash relief agents, such as methylbenzethonium chloride and the like; emollients and moisturizers, such as mineral oil, PEG-4 dilaurate, lanolin oil, petrolatum, mineral wax and the like; fungicides, such as butocouazole nitrate, haloprogen, clotrimazole, and the like; herpes treatment drugs, such as O-[(2-hydroxyethoxy)-methyl]guanine; pruritic medications, such as alcometasone dipropionate, betamethasone valerate, isopropyl myristate MSD, and the like; psoriasis, seborrhea ad scabicide agents, such as anthralin, methoxsalen, coal tar and the like; steroids, such as 2-(acetyloxy)-9-fluoro-1',2',3',4'-tetrahydro-11-hydroxypregna-1,4-dieno[16,17-b]naphthalene3,20-dione and 21-chloro-9-fluro-1',2',3',4'-tetrahydro-11b-hydroxypregna-1,4-dienol[16z,17-b]naphthalene-3,20-dione. Any other medication capable of topical administration also can be incorporated in a composition of the present invention in an amount sufficient to perform its intended function. Other topically active compounds are listed in *Remington's Pharmaceutical Sciences*, 17th Ed., Merck Publishing Co, Easton, Pa. (1985), pages 773–791 and pages 1054–1048 (hereinafter *Remington's*), incorporated herein by reference.

An above-described first topically active compound is designed to remain on the skin or hair to perform its intended function. However, in particular situations, a first topically active compound that is rinsed from the skin or hair can be incorporated into the internal aqueous $W_1$ phase of the primary emulsion.

For example, a $W_1$-O-$W_2$ multiple emulsion composition designed as a permanent wave composition can incorporate a reducing agent into the external aqueous phase as the second topically active compound. After applying the $W_1$-O-$W_2$ composition to the hair and allowing the composition to contact the hair for a sufficient time to reduce the hair, the external aqueous phase is rinsed from the hair leaving droplets of the primary emulsion on the hair.

The primary emulsion has incorporated therein an oxidizing agent as the first topically active compound. After the oil phase, and preferably a volatile oil phase, evaporates from the primary emulsion, the oxidizing agent is released to neutralize the hair and any reducing agent remaining on the hair. Excess oxidizing agent then can be rinsed from the hair in a second rinsing step.

Exemplary, but non-limiting, oxidizing agents used as the first topically active compound are ammonium persulfate, hydrogen peroxide, potassium bromate, potassium chromate, potassium persulfate, sodium bromate, sodium carbonate, peroxide, sodium iodate, sodium perborate, sodium persulfate, urea peroxide, and mixtures thereof. An oxidizing agent also can be the second topically active compound when the first topically active compound is a hair conditioner. In addition, the second topically active compound can be a bleaching agent (i.e., an oxidizing agent) and the first topically active compound can be a hair dye.

In preferred embodiments of the invention, the topically active compound should not be cationic in nature, particularly if anionic surfactants are used.

Water

Sufficient water is present in the aqueous phase such that the aqueous phase comprises about 1% to about 99% by weight of the $W_1O$. Total water present in the $W_1$-O-$W_2$ multiple emulsion composition is about 30% to about 99.9%, and typically about 40% to about 95%, by weight of the composition.

Solutes

The internal aqueous phase must also include oil-insoluble solute(s). The solutes are introduced to balance osmotic pressure. Among solutes which may be added are organic or inorganic salts such as alkali metal chlorides, sulfates, nitrates, benzoates and acetates and sugars and sugar derivatives, for example glucose and sucrose. Solute, when added to the internal aqueous phase, comprises 0.01 to 30% by wt., preferably 0.1 to 20%, most preferably 0.5 to 15%.

Optionals

It is also possible to add surfactant to the internal aqueous phase though this is added generally to the external $W_2$ phase. The surfactant can be any of the surfactants discussed in connection with the $W_2$ phase below.

The internal aqueous phase also can include optional ingredients traditionally included in topically applied compositions. These optional ingredients include, but are not limited to, dyes, fragrances, preservatives, antioxidants, detackifying agents, and similar types of compounds. The optional ingredients are included in the internal aqueous phase of the primary emulsion in an amount sufficient to perform their intended function.

O Phase

The primary $W_1$/O emulsion also comprises about 0.5% to about 99%, preferably about 0.75% to about 80%, and most preferably about 1% to about 70%, by weight of the emulsion of an oil phase. The oil phase is comprised of an oil (discussed below) and a low HLB surfactant (discussed below). The oil phase encapsulates the internal aqueous $W_1$ phase of the primary emulsion to form droplets of about 0.1 to about 1,000$\mu$, and preferably about 1 to about 500$\mu$, in diameter. The oil phase therefore provides a barrier between the internal aqueous phase of the primary emulsion and the external aqueous phase of the $W_1$-O-$W_2$ multiple emulsion composition. The oil phase provides a sufficient barrier even though the oil phase constitutes as little as 0.5% by weight of the $W_1O$ emulsion.

Oil

The oil may be volatile (except for silicone) or nonvolatile.

A volatile oil may comprise a volatile hydrocarbon oil which evaporates during the process of drying skin or hair, and thereby releases the internal aqueous $W_1$ phase, which includes the first topically active compound to contact the skin or hair. This oil preferably should contain no volatile silicone since volatile silicones tend to destabilize the multiple emulsion.

In one embodiment, the oil may comprise a combination of a volatile oil (except for silicone) and a nonvolatile oil. In this embodiment, an oil can be designed to evaporate at a pre-selected temperature and provide a controlled release of the first topically active compound at the pre-selected temperature. Pre-selected temperatures are those encountered during normal hair drying, provided by a hair dryer, or provided by a curling iron.

As previously stated, the oil also can include a water insoluble topically active compound in a sufficient amount to impart a particular functional or esthetic effect (e.g., emolliency), as long as the topically active compound does not adversely affect the $W_1$-O-$W_2$ multiple emulsion composition (e.g., does not impart emulsion instability).

Although the oil can incorporate a topically active compound, the topically active compound preferably is incorporated into the internal aqueous phase.

The volatile oil preferably comprises a volatile hydrocarbon compound, such as a hydrocarbon having about 10 to about 30 carbon atoms, that has sufficient volatility to slowly volatilize from the skin or hair after application of the $W_1$-O-$W_2$ multiple emulsion composition to the skin or hair and subsequent rinsing. A preferred volatile hydrocarbon compound is an aliphatic hydrocarbon having about 12 to about 24 carbon atoms, and having a boiling point of about 100° C. to about 250° C. The volatile hydrocarbon compounds perform the same function and provide essentially the same benefits as the volatile silicone compounds.

Volatile hydrocarbon compounds incorporated into the primary emulsion include, for example, isododecane and isohexadecane, i.e., PERMETHYL 99A, PERMETHYL 101A and PERMETHYL 102A, available from Presperse, Inc., South Plainfield, N.J. Other exemplary volatile hydrocarbon compounds are depicted in general structural formula (I), wherein m ranges from 2 to 5.

(I)

Another exemplary volatile hydrocarbon compound is ISOPAR M (a $C_{13}$–$C_{14}$ isoparaffin available from Exxon Chemical Co., Baytown, Tex). Preferably, the volatile hydrocarbon is less than 50% unsaturated.

As previously stated, the oil also can be a nonvolatile oil. The nonvolatile oil comprises a nonvolatile silicone compound, a nonvolatile hydrocarbon, or a mixture thereof. Preferably, the nonvolatile oil comprises compounds which contain less than 50% unsaturation. The nonvolatile oil phase does not evaporate from the skin or hair. The first topically active compound therefore is released by rubbing the skin or hair to rupture the $W_1$/O emulsion. A nonvolatile oil has a boiling point at atmospheric pressure of greater than about 250° C.

Exemplary nonvolatile silicone compounds include a polyalkyl siloxane, a polyaryl siloxane or a polyalkylaryl siloxane. Mix of these nonvolatile silicone compounds also are useful. The nonvolatile silicones are nonfunctional siloxanes or siloxane mixtures having a viscosity of about 10 to about 600,000 cs, and typically about 350 to about 10,000 cs, at 25° C. The so-called "rigid silicones", as described in U.S. Pat. No. 4,902,499, herein incorporated by reference, having a viscosity above 600,000 cs at 20° C., and a weight average molecular weight of at least about 500,000, also are useful in a composition of the present invention. A phenyltrimethicone also is useful as a nonvolatile silicone compound.

The preferred nonvolatile silicone compound is a nonvolatile polydimethylsiloxane compound, such as a mixture, in about a 2:1 weight ratio, of a low molecular weight polydimethylsiloxane fluid and a higher molecular weight polydimethylsiloxane gum. Preferred silicone gums include linear and branched polydimethylsiloxanes of the following general formula:

$(CH_3)_3SiO$—$[Si(CH_3)_2O]_n$—$Si(CH_3)_3$, wherein n is a number from about 2,000 to about 15,000, and preferably from about 2,000 to about 7,000. Silicone gums useful in compositions of the present invention are available from a variety of commercial sources, including General Electric Company, Waterford, N.Y. and Dow Corning Corp., Midland, Mich.

The nonvolatile oil also can comprise a nonvolatile hydrocarbon compound, such as mineral oil. Other exemplary nonvolatile hydrocarbon compounds that can be used as the oil include, but are not limited to, a branched 1-decene oligomer, like 1-decene dimer or a polydecene.

The oil also optionally can comprise (1) an oil, such as jojoba oil, wheat germ oil or purcellin oil; or (2) a water insoluble emollient, such as, for example, an ester having at least about 10 carbon atoms, and preferably about 10 to about 32 carbon atoms.

Suitable esters include those comprising an aliphatic alcohol having about eight to about twenty carbon atoms and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight chained or branched. Preferably, the ester has a molecular wt. of less than about 500. Suitable esters therefore include, for example, but are not limited to:

(a) aliphatic monohydric alcohol esters, including but not limited to:
  myristyl propionate,
  isopropyl isostearate,
  isopropyl myristate,
  isopropyl palmitate,
  cetyl acetate,
  cetyl propionate,
  cetyl stearate,
  isodecyl neopentanotate,
  cetyl octanoate,
  isocetyl stearate;
(b) aliphatic di- and tri-esters of polycarboxylic acids, including but not limited to:
  diisopropyl adipate,
  diisotstearyl fumarate,
  dioctyl adipate, and
  triisostearyl citrate;
(c) aliphatic polyhydric alcohol esters, including but not limited to:
  propylene glycol dipelargonate;
(d) aliphatic esters of aromatic acids, including but not limited to:
  $C_{12}$–$C_{15}$ alcohol esters of benzoic acid,
  octyl salicylate,
  sucrose benzoate, and
  dioctyl phthalate.

Numerous other esters are listed in the *CTFA Handbook* at pages 24 through 26, incorporated herein by reference.

Low HLB Emulsifier

The O phase of the present invention also includes about 0.1% to about 30%, and preferably about 1% to about 15% on the weight of the oil of a low HLB emulsifier.

The low HLB emulsifier may comprise a silicon-free surfactant, or a blend of silicon-free surfactants, having an HLB value of about less than 10 (i.e., an HLB value of about 0.1 to about less than 10), an oil-soluble silicon-based surfactant, an oil-soluble polymeric surfactant, or mixtures thereof. Preferably, the silicon-free surfactant or surfactant blend has an HLB value of about 1 to about 7. To achieve the full advantage of the present invention, the silicon-free surfactant or surfactant blend has an HLB value of about 3 to about 6. The term "oil-soluble" as used herein means a compound having a solubility of at least 0.1 g per 100 ml of oil phase to form a true solution.

The HLB value of a particular surfactant can be found in *McCutcheon's* Emulsifiers and Detergents, North American and International Editions, MC Publishing, Glen Rock, N.J. (1993) (hereinafter McCutcheon's). Alternatively, the HLB value of a particular surfactant can be estimated by dividing the weight percent of oxyethylene in the surfactant by five (for surfactants including only ethoxy moieties). In addition, the HLB value of a surfactant blend can be estimated by the following formula:

HLB=(wt. % A)(HLB$_A$)+(wt. % B)(HLB$_B$), wherein wt. % A and wt. % B are the weight percent of surfactants A and B in the silicon-free surfactant blend, and HLB$_A$ and HLB$_B$ are the HLB values for surfactants A and B, respectively.

Low HLB surfactant can be a silicone-based surfactant or silicone free surfactant.

Exemplary classes of silicon-free nonionic surfactants include, but are not limited to, polyoxyethylene ethers of fatty ($C_6$–$C_{22}$) alcohols, polyoxyethylene/polyoxypropylene ethers of fatty ($C_6$–$C_{22}$) alcohols, ethoxylated alkylphenols, polyethylene glycol ethers of methyl glucose, polyethylene glycol ethers of sorbitol, and mixtures thereof.

Exemplary silicon-free nonionic surfactants are the ethoxylated alcohols having an HLB value of about 0.1 to about 10. An especially preferred ethoxylated alcohol is laureth-1, i.e., lauryl alcohol ethoxylated with an average of one mole of ethylene oxide. Other suitable ethoxylated alcohols include laureth-2, laureth-3 and laureth-4. Numerous other nonionic surfactants having an HLB of about 0.1 to about 10 are listed in McCutcheon's at pages 229–236, incorporated herein by reference. Other exemplary silicon-free nonionic surfactants having an HLB value of about 0.1 to about 10 include, but are not limited to, the ethoxylated nonylphenols, ethoxylated octylphenols, ethoxylated dodecylphenols, ethoxylated fatty ($C_6$–$C_{22}$) alcohols having four or fewer ethylene oxide moieties, oleth-2, steareth-3, steareth-2, ceteth-2, oleth-3, and mixtures thereof.

The emulsifier can also comprise a silicon-free surfactant blend having an HLB value of about 1 to about 10. The blend is a mixture of a sufficient amount of a surfactant having allow HLB value, i.e., about 0.1 to about 10, and a sufficient amount of a surfactant having a higher HLB value, i.e., about 1 to greater than about 10, such that the surfactant blend has an HLB value of about 1 to about 10. Exemplary, but non-limiting, nonionic surfactants having a high HLB value are listed in *McCutcheon's* at pages 236–246, incorporated herein by reference.

A preferred silicone free surfactant is PEG 30 dipolyhydroxystearate.

An exemplary oil-soluble silicon-based surfactant is a dimethicone copolyol, which is a dimethylsiloxane polymer having polyoxyethylene and/or polyoxypropylene side chains, such as DOW CORNING 3225C and 5225C FORMULATION AID, available from Dow Corning Co., Midland, Mich. The dimethicone copolyol has about or fewer ethylene oxide and/or propylene oxide monomer units, in total, in the side chains. Dimethicone copolyols conventionally are used in conjunction with silicones because the silicon-containing surfactants are extremely soluble in a volatile or a nonvolatile silicone compound, are extremely insoluble in water, and have a low skin irritancy potential.

Another exemplary, but non-limiting, oil-soluble, silicon-based surfactant is an alkyl dimethicone copolyol, such as cetyl dimethicone copolyol available commercially as ABIL® EM 90 from Goldschmidt Chemical Corporation, Hopewell, Va. The alkyl dimethicone copolyols have the structure:

wherein:

p is a numeral from 7 through 17;

q is a numeral from 1 through 100;

m is a numeral from 1 through 40;

n is a numeral from 0 through 200; and

PE is $(C_2H_4O)_a(C_3H_6O)_b$—H having a molecular weight of about 250 to about 2000, wherein a and b are selected such that the weight ratio of $C_2H_4O/C_3H_6O$ is from 100/0 to 20/80.

The surfactant phase also can comprise an oil-soluble polymeric surfactant. Polymeric surfactants capable of forming water-in-oil emulsions completely cover the surface of the water droplet, are firmly anchored at the oil-water interface, the external oil phase is a good solvent for the stabilizing portion of the polymeric surfactant, and the thickness of the polymer layer on the oil side of the interface is sufficient to ensure stability. These surfactants may include ethoxy, propoxy and/or similar alkylene oxide monomer units, e.g., butoxy. The oil-soluble polymeric surfactants act as surfactants and are not physically or chemically cross-linked in solution. The oil-soluble polymeric surfactants therefore are differentiated from polymeric gelling agents such as polyacrylic acid or polymethacrylic acid.

Accordingly, exemplary oil-soluble polymeric surfactants include, but are not limited to, polyoxyethylene-polyoxypropylene block copolymers, and similar polyoxyalkylene block copolymers. The oil-soluble block copolymers typically have less than about 20% by weight of ethylene oxide. Specific non-limiting oil-soluble polymeric surfactants include Poloxamer 101, Poloxamer 105, PPG-2-Buteth-3, PPG-3-Butech-5, PPG-5-Butech-7, PPG-7-Butech-10, PPG-9-Buteth-12, PPG-12-Buteth-16, PPG-15-Buteth-20, PPG-20-Buteth-30, PPG-24-Buteth-27, PPG-28-Buteth-35, and PEG-15 Butanediol. Other useful oil-soluble polymeric surfactants are polyamines, i.e., polyoxyethylene-polyoxypropylene block copolymers of ethylene diamine, having less than about 40% by weight ethylene oxide.

In accordance with an important feature of the present invention, the hydrophobic moiety of a silicon-free surfactant, silicon-containing surfactant or polymeric surfactant is sufficiently soluble in the oil phase such that a sufficient amount of the surfactant is present in the oil phase to stabilize the primary $W_1/O$ emulsion. In one embodiment when the oil phase comprises a silicone compound, the surfactant phase comprises either a silicon-based surfactant, a silicon-free surfactant having a hydrophobic moiety preferably containing about ten to about fourteen carbon atoms, an oil-soluble polymeric surfactant, or a mixture thereof. If the hydrophobic moiety of the silicon-free surfactant is saturated and includes more than about 14 carbon atoms, the silicon-free surfactant is insoluble in the silicone phase and the primary $W_1/O$ emulsion is unstable. If the hydrophobic moiety includes less than about 10 carbon atoms, the primary $W_1/O$ emulsion has a tendency to coalesce i.e., the emulsion droplets fuse to form large droplets. The amount of surfactant phase necessary to provide a primary emulsion of desired $W_1/O$ droplet diameter varies with the amount of aqueous phase in the primary emulsion and is easily determined by those skilled in the art.

One particularly preferred emulsifier is cetyl dimethicone copolyol.

The External Aqueous Phase

The external aqueous phase ($W_2$) of the $W_1$-O-$W_2$ multiple emulsion comprises an isotropic mixture of surfactants phase (as opposed to lamellar phase of U.S. Pat. No. 5,656,280).

As noted, this external phase comprises a non-amido anionic surfactant and/or other surfactant. Preferably, it comprises anionic in combination with amphoteric surfactants wherein the nonamido group anionic comprises 1 to 99% of the surfactant system and amphoteric comprises 1 to 99% of the surfactant system. The key to the invention is that much greater levels of surfactants can be used than previously believed possible while maintaining a multiple emulsion.

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

wherein $R^4$ ranges from $C_8$–$C_{22}$ alkyl and M is a solubilizing cation and M is defined as above;

Also included are the alkoxylated citrate sulfosuccinates; and alkoxylated sulfosuccinates such as the following:

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R—(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In general the anionic component will comprise from about 1 to 30% by weight of the composition, preferably 2 to 25%, most preferably 5 to 20% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They should generally include an alkyl or alkenyl group of 7 to 18 carbon atoms.

Suitable amphoteric detergents within the above general formula include simple betaines of formula:

where $R^1$ is alkyl or alkenyl of 7 to 18 carbons; $R^2$ and $R^3$ are each independently alkyl, hydroxyalkyl or carboxyalkyl of 2 to 3 carbon atoms.

$R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula or where m is 2 or 3, or variants of these in which —$(CH_2)_3$SO$^-_3$ is replaced by In these formulae $R^1$, $R^2$ and $R^3$ are as discussed previously.

The amphoteric/zwitterionic generally comprises about 1 to 30% by weight, preferably 2 to 25% of the composition, more preferably 5 to 20%.

In addition to one or more anionic and amphoteric and/or zwitterionic, the surfactant system may optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Lienado, both of which are also incorporated into the subject application by reference.

Preferred alkyl polysaccharides are alkylpolyglycosides of the formula wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic comprises 0 to 10% by wt. of the composition.

The following examples are intended to further illustrate the invention and are not intended to limit the invention in any way.

All percentages used, unless indicated otherwise, are intended to be percentages by weight.

Definition and Measurement of Stability

Sodium ISE: To measure multiple emulsion stability, a sodium ion sensitive electrode (Coming 476138) was attached to an Orion EA 920 expandable ion analyzer.

The multiple emulsion samples were intentionally prepared with a "too low" internal NaCl concentration. Thus, the Na ion concentration of the separated bottom phase served as a rapid indicator of multiple emulsion stability.

In the case of multiple emulsion breakage, the NaCl from the internal phase is released and the NaCl concentration in the external aqueous phase increases because the initial salt concentration is greater in the internal phase. A plot of separated phase sodium ion concentration versus storage time shows a positive slope (increasing Na ion concentration over time).

In the case of a stable multiple emulsion, the NaCl is held in the internal phase and only water is released to the external phase. A plot of separated phase sodium ion concentration versus storage time shows a negative slope (gradual Na ion dilution over time) or virtually no slope (water was released at an early stage).

5 g of the separated external aqueous (bottom) phase was taken from the separatory funnel and diluted to 50 g with 45 g of milli-Q water. To this was added 50 g of 0.5 M triethanolamine (TEA) to maintain ionic strength and equalize activity coefficients.

Standards were prepared by taking 1,2, 3, 4 and 5 g samples of the original external phase and diluting them with 49, 48, 47, 46, and 45 g of milli-Q water, respectively, to 50 g. 50 g of 0.5 M TEA was added to each sample, as above.

Each of the standard samples and the separated emulsion sample were measured for sodium ion activity (concentration) using the sodium ion sensitive electrode.

Those multiple emulsions which showed a zero or negative slope over the course of 30 days at room temperature (20–25° C.) storage were deemed "stable". Conversely, those which displayed a positive slope over the same amount of time were deemed "unstable".

Multiple Emulsion Preparation
Primary ($W_1/O$) Emulsions
Oil Phase: The oil and the oil soluble surfactant (low HLB emulsifier) were mixed together at room temperature using overhead stirring.

Internal aqueous phase ($W_1$): Sodium chloride solutions with or without topically active compounds of appropriate concentrations were prepared and the pH was adjusted to 7.0.

$W_1/O$ preparation: the oil phase (O) was charged into the vessel. The salt/topically active compound solution ($W_1$) was added to the oil phase steadily through the addition funnel over the course of 10–12 minutes while mixing with the side scraper (60–80 rpm). Slow addition of aqueous phase under low shear mixing is essential to obtain a stable primary emulsion. Upon complete addition of the aqueous phase, the mixing speed of the side scraper was reduced to 40 rpm and the homogenizer was turned on. Homogenization was carried out for 3 minutes each at 8000, 9500 and 13,500 rpm at room temperature. The heat generated during the homogenization process raised the temperature of the batch to ~35° C.

Multiple Emulsion
External aqueous phase ($W_2$): External aqueous phases were prepared in a jacketed vessel by mixing the minority surfactant into the majority surfactant at 60° C. with intense mixing. The pH of each surfactant solution was pre-adjusted to 7.0. Surfactant solutions which had a gel like consistency were centrifuged at 7000 rpm for 20 minutes to remove the entrapped air.

$W_1/O/W_2$ preparation: The primary emulsion ($W_1/O$) was charged into the smaller scale vessel followed by addition of the external aqueous phase ($W_2$). The mixture was hand-mixed gently for 15 seconds using a spatula. This was followed by mixing with the side-scraper for 8 minutes at 70–105 rpm (higher speed was used when mixing at lower speed was found to be inadequate). A small spatula was inserted into the vessel as a baffle to ensure good mixing around the center spindle of the side scraper. The resulting multiple emulsions were transferred into 250 ml separatory funnels to await separation of the aqueous phase for emulsion stability analysis.

EXAMPLES

The following components were used in the experiment as follows;

| Phase | Material | Supplier | Trade name | Function |
|---|---|---|---|---|
| W1 | Milli-Q Water | | | |
| | Sodium Chloride | Fisher | | Internal Solute |
| | Lactic Acid | Fluka | | Benefit Agent |
| | Glucose | Aldrich | | Benefit Agent |
| | Potassium Hydroxide | Fisher | | |
| | Polyquaternium 11 | ISP Corp. | GAFQUAT 755N | Hair Styling Polymer |
| | Poly(vinylpyrrolidone) | ISP Corp. | PVP K-120 | Hair Styling Polymer |
| (O)il | Light Mineral (Paraffin) Oil | Fisher | | Emollient |
| | Heavy Mineral (Paraffin) Oil | Fisher | | Emollient |
| | Sunflower Oil | Clark/Welch | | Emollient |
| | Octyl Palmitate | Goldschmidt | Tegosoft OP | Emollient |
| | Non volatile Silicone (Dimethicone) Oil | Dow Corning | DC 200 Fluid 50 cst | Emollient |
| | Cetyl dimethicone copolyol | Goldschmidt | Abil EM 90 | Low HLB surf. |
| W2 | Cocoamidopropyl betaine | Goldschmidt | Tego Betain F 50 | Amphoteric High HLB surf. |
| | Cocoamphoglycinate | McIntyre | Mackam 1C | Amphoteric High HLB surf. |
| | Sodium laureth sulfate (SLES) | Stepan | Steol CS-330L | Anionic High HLB Surfactant |
| | Sodium lauryl sulfate (SDS) | Fluka | | Anionic High HLB Surfactant |
| | Sodium cocoyl isethionate | PPG Indust. | Jordapon CI | Anionic High HLB Surfactant |
| | Alkanol carboxylate | Shell | Neodox 23-4 | Anionic High HLB Surfactant |
| | Lauryl ether sulfosuccinate | McIntyre | Mackanate EL | Anionic High HLB Surfactant |
| | Disodium cocamido MEA sulfosuccinate | McIntyre | Mackanate CM | Anionic High HLB Surfactant |
| | Disodium cocamido MIPA sulfosuccinate | McIntyre | Mackanate CP | Anionic High HLB Surfactant |
| | Acylamine polyglycol ether sulfate | Hoechst AG | Genapol AMS | Anionic High HLB Surfactant |
| | Decyl polyglucose | Henkel/Emery | Plantaren 2000 | Nonionic High HLB Surfactant |

Examples 1–14

In order to show effect of varying anionics in mixture with amphoterics (e.g., betaine) on multiple emulsion stability, the following examples were prepared:

TABLE 1

Effect of different anionics in mixture with betaine on multiple emulsion stability

| | Formula # | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| W1 Phase | | | | | | | | | | | | | | |
| Water | 40.3 | 39.9 | 40.3 | 39.9 | 39.9 | 39.9 | 39.9 | 40.3 | 39.9 | 40.3 | 39.9 | 40.3 | 39.9 | 39.5 |
| Sodium Chloride | 1.7 | 2.1 | 1.7 | 2.1 | 2.1 | 2.1 | 2.1 | 1.7 | 2.1 | 1.7 | 2.1 | 1.7 | 2.1 | 2.5 |
| (O)il Phase | | | | | | | | | | | | | | |
| Light Paraffin Oil | 16.2 | 16.2 | 16.2 | 16.2 | 16.2 | 16.2 | 16.2 | 16.2 | 16.2 | 16.2 | 16.2 | 16.2 | 16.2 | 16.2 |
| Cetyl dimethicone copolyol | 1.8 | 1.8 | 1.8 | 1.8 | 1.8 | 1.8 | 1.8 | 1.8 | 1.8 | 1.8 | 1.8 | 1.8 | 1.8 | 1.8 |
| W2 Phase | | | | | | | | | | | | | | |
| Water | 26.4 | 26.4 | 25 | 25 | 28.6 | 28.6 | 28.6 | 25 | 25 | 25 | 25 | 25 | 25 | 25 |
| Cocamidopropyl betaine | 8.2 | 8.2 | 9 | 9 | 6.8 | 6.8 | 6.8 | 9 | 9 | 9 | 9 | 9 | 9 | 9 |
| Sodium laureth sulfate | 5.4 | 5.4 | | | | | | | | | | | | |
| Sodium lauryl sulfate | | | 6 | 6 | | | | | | | | | | |
| Sodium cocoyl isethionate | | | | | 4.6 | | | | | | | | | |
| Alkanol carboxylic acid | | | | | | 4.6 | | | | | | | | |
| Lauryl ether sulfosuccinate | | | | | | | 4.6 | | | | | | | |
| Disodium cocamido MEA sulfosuccinate | | | | | | | | 6 | 6 | | | | | |
| Disodium cocamide MPA sulfosuccinate | | | | | | | | | | 6 | 6 | | | |
| Acylaminopolyglycol ether sulfate | | | | | | | | | | | | 6 | 6 | 6 |
| Total | 100 | 100 | 100 | 100 | 100 | 100 | 100 | 100 | 100 | 100 | 100 | 100 | 100 | 100 |
| Stability of Multiple emulsion after 30 days at room temperature | Stable | Stable | Stable | Stable | Stable | Stable | Stable | Unstable | Unstable | Unstable | Unstable | Unstable | Unstable | Unstable |

As clearly seen, anionic surfactants with amido group render the multiple emulsion unstable (Examples 8 to 14 compared to 1 to 7).

Examples 15–21

In order to determine effect, if any, of amphoteric/anionic ratio on stability, the following examples were prepared:

As noted, regardless of amphoteric/anionic ratio, emulsion was stable.

Examples 1 and 22

From the following examples, it can be seen that multiple emulsion may be stable over various types of amphoterics.

TABLE 2

Effect of amphoteric/anionic ratio on multiple emulsion stability

| | Formula # | | | | | | | | |
|---|---|---|---|---|---|---|---|---|---|
| | 15 | 16 | 17 | 18 | 1 | 2 | 19 | 20 | 21 |
| W1 Phase | | | | | | | | | |
| Water | 40.3 | 39.9 | 38.2 | 39.9 | 40.3 | 39.9 | 40.7 | 41.8 | 41.8 |
| Sodium Chloride | 1.7 | 2.1 | 3.8 | 2.1 | 1.7 | 2.1 | 1.3 | 0.2 | 0.2 |
| (O)il Phase | | | | | | | | | |
| Light Paraffin Oil | 16.2 | 16.2 | 16.2 | 16.2 | 16.2 | 16.2 | 16.2 | 16.2 | 16.2 |
| Cetyl dimethicone copolyol | 1.8 | 1.8 | 1.8 | 1.8 | 1.8 | 1.8 | 1.8 | 1.8 | 1.8 |
| W2 Phase | | | | | | | | | |
| Water | 28.6 | 28.6 | 28.6 | 28.6 | 26.4 | 26.4 | 28.6 | 28.6 | 28.6 |
| Cocamidopropyl betaine | 11.4 | 11.4 | 11.4 | 9.1 | 8.2 | 8.2 | 4.6 | 2.3 | |
| Sodium laureth sulfate | | | | 2.3 | 5.4 | 5.4 | 6.8 | 9.1 | 11.4 |
| Total | 100 | 100 | 100 | 100 | 100 | 100 | 100 | 100 | 100 |
| Stability of Multiple Emulsion after 30 days at room temperature | Stable | Stable | Stable | Stable | Stable | Stable | Stable | Stable | Stable |

TABLE 3

Effect of different amphoterics with anionic on multiple emulsion stability

| | | Formula # | |
|---|---|---|---|
| | | 1 | 22 |
| W1 Phase | Water | 40.3 | 40.7 |
| | Sodium Chloride | 1.7 | 1.3 |
| (O)il Phase | Light Paraffin Oil | 16.2 | 16.2 |
| | Cetyl dimethicone copolyol | 1.8 | 1.8 |
| W2 Phase | Water | 26.4 | 26.4 |
| | Cocamidopropyl betaine | 8.2 | |
| | Cocoamphoglycinate | | 6.8 |
| | Sodium laureth sulfate | 5.4 | 4.6 |
| Total | | 100 | 100 |
| Stability of | Multiple Emulsion after 30 days at room temperature | Stable | Stable |

Examples 23 and 24

The following compositions were prepared to show that nonionics and amphoterics also form stable multiple emulsions

TABLE 4

Effect of nonionics with amphoteric on multiple emulsion stability

| | | Formula # | |
|---|---|---|---|
| | | 23 | 24 |
| W1 Phase | Water | 40.3 | 39.9 |
| | Sodium Chloride | 1.7 | 2.1 |
| (O)il Phase | Light Paraffin Oil | 16.2 | 16.2 |
| | Cetyl dimethicone copolyol | 1.8 | 1.8 |
| W2 Phase | Water | 25 | 25 |
| | Cocamidopropyl betaine | 9 | 9 |
| | Decyl polyglucose | 6 | 6 |
| Total | | 100 | 100 |
| Stability of | Multiple Emulsion after 30 days at room temperature | Stable | Stable |

Examples 1 and 25–28

From the following table, it can be seen that stable multiple emulsions are formed when the composition of the oil phase is less than 50% unsaturated hydrocarbon compounds, i.e. sunflower oil has a composition which is greater than 50% unsaturated hydrocarbon compounds.

TABLE 5

Effect of different oils on multiple emulsion stability

| | | Formula # | | | | |
|---|---|---|---|---|---|---|
| | | 1 | 25 | 26 | 27 | 28 |
| W1 Phase | Water | 40.3 | 40.3 | 41.6 | 40.3 | 41.6 |
| | Sodium Chloride | 1.7 | 1.7 | 0.4 | 1.7 | 0.4 |
| (O)il Phase | Light Paraffin Oil | 16.2 | | | | |
| | Heavy Paraffin Oil | | 16.2 | | | |
| | Octyl Palmitate | | | 16.2 | | |
| | Non volatile Dimethicone Oil | | | | 16.2 | |
| | Sunflower Oil | | | | | 16.2 |
| | Cetyl dimethicone copolyol | 1.8 | 1.8 | 1.8 | 1.8 | 1.8 |
| W2 Phase | Water | 26.4 | 26.4 | 26.4 | | 26.4 |
| | Cocamidopropyl betaine | 8.2 | 8.2 | 8.2 | | 8.2 |
| | Sodium laureth sulfate | 5.4 | 5.4 | 5.4 | | 5.4 |
| Total | | 100 | 100 | 100 | 100 | 100 |
| Stability of | Multiple Emulsion after 30 days at room temperature | Stable | Stable | Stable | Stable | Un-stable |

Examples 29–31

In order to show the effect of low HLB emulsifier concentration, the following examples were prepared.

TABLE 6

Effect of emulsifier concentration on multiple emulsion stability

| | | Formula # | | |
|---|---|---|---|---|
| | | 29 | 30 | 31 |
| W1 Phase | Water | 38.2 | 38.2 | 38.2 |
| | Sodium Chloride | 3.8 | 3.8 | 3.8 |
| (O)il Phase | Light Paraffin Oil | 17.1 | 16.2 | 14.4 |
| | Cetyl dimethicone copolyol | 0.9 | 1.8 | 3.6 |
| W2 Phase | Water | 26.4 | 26.4 | 26.4 |
| | Cocamidopropyl betaine | 8.2 | 8.2 | 8.2 |
| | Sodium laureth sulfate | 5.4 | 5.4 | 5.4 |
| Total | | 100 | 100 | 100 |
| Stability of | Multiple Emulsion after 30 days at room temperature | Un-stable | Stable | Stable |

Examples 2, 32 and 33

To show whether multiple emulsions are stable over broad composition of surfactant/oil ratios, the following examples were prepared:

TABLE 7

Effect of total surfactant/oil ratio on multiple emulsion stability

| | | Formula # | | |
|---|---|---|---|---|
| | | 2 | 32 | 33 |
| W1 Phase | Water | 39.9 | 20 | 6.7 |
| | Sodium Chloride | 2.1 | 1.1 | 0.4 |
| (O)il Phase | Light Paraffin Oil | 16.2 | 8.1 | 2.7 |
| | Cetyl dimethicone copolyol | 1.8 | 0.9 | 0.3 |
| W2 Phase | Water | 26.4 | 46.1 | 59.3 |
| | Cocamidopropyl betaine | 8.2 | 14.3 | 18.4 |
| | Sodium laureth sulfate | 5.4 | 9.5 | 12.2 |
| Total | | 100 | 100 | 100 |
| Stability of | Multiple Emulsion after 30 days at room temperature | Stable | Stable | Stable |

As clearly seen, the stability remained over a broad range of surfactant/oil ratios.

Examples 2, 34–37

In order to show the stability of the multiple emulsion when a skin benefit agent or hair styling polymer is incorporated into the $W_1$ phase, Compositions 2 and 34–37 were prepared.

TABLE 8

Effect of incorporating benefit agent (lactic acid) into W1 phase on multiple emulsion stability

| | Formula # | | | | |
|---|---|---|---|---|---|
| | 2 | 34 | 35 | 36 | 37 |
| W1 Phase | | | | | |
| Water | 39.9 | 36.5 | 36.9 | 24.5 | 26.6 |
| Sodium Chloride | 2.1 | 2.1 | 2.1 | 0.7 | 0.7 |
| Lactic Acid | | 2.1 | | | |
| Potassium Hydroxide | | 1.3 | | | |
| Glucose | | | 3 | | |
| Polyquaternium 11 | | | | 2.8 | |
| Poly(vinylpyrrolidone) | | | | | 0.7 |
| (O)il Phase | | | | | |
| Light Paraffin Oil | 16.2 | 16.2 | 16.2 | 10.8 | 10.8 |
| Cetyl dimethicone copolyol | 1.8 | 1.8 | 1.8 | 1.2 | 1.2 |
| W2 Phase | | | | | |
| Water | 26.4 | 24.5 | 24.4 | 42 | 42 |
| Cocamidopropyl betaine | 8.2 | 7.4 | 8.2 | | |
| Sodium laureth sulfate | 5.4 | 4.9 | 5.4 | | |
| Sodium lauryl sulfate | | | | 18 | 18 |
| Lactic Acid | | 2 | | | |
| Potassium Hydroxide | | 1.2 | | | |
| Glucose | | | 2 | | |
| Total | 100 | 100 | 100 | 100 | 100 |
| Stability of Multiple Emulsion after 30 days at room temperature | Stable | Stable | Stable | Unstable* | Stable* |

*= determined by optical microscopy

As clearly seen, in Examples 34 and 35, incorporation of benefit agent had no effect on multiple emulsion stability. Examples 36 and 37 demonstrate the criticality that if a cationic hair styling polymer is used in systems containing an anionic surfactant, multiple emulsion stability will be adversely affected.

What is claimed is:

1. A $W_1$-O-$W_2$ multiple emulsion comprising:
    (1) about 1% to 99% by wt. of the composition of a $W_1$/O emulsion comprising;
        (a) about 1% to 99% of said emulsion of an internal aqueous phase comprising (i) water; (ii) 0.01 to 30% by wt. emulsion solute; and (iii) 0–30% optional surfactant;
        (b) about 0.5% to about 99% of the emulsion of an oil phase surrounding said internal aqueous phase wherein said oil is selected from the group consisting of volatile hydrocarbon, nonvolatile hydrocarbons, nonvolatile silicones and mixtures thereof;
        (c) about 0.1 to about 20% by wt. emulsion of a surfactant emulsifier selected from the group consisting of a silicon-free surfactant or surfactant blend having an HLB value of about 10 or less, an oil soluble silicon based surfactant, an oil-soluble polymeric surfactant and mixture thereof; and
        (d) an optional and topically effective amount of a first topically active compound, which may be found in either the aqueous phase (a), oil phase (b) or both; and
    (2) about 1 to 99% by wt. of an external isotropic aqueous phase $W_2$ comprising:
        (a) 2 to 80% by wt. aqueous phase of a surfactant phase which comprises a non-amido anionic or nonionic or mixture of two in combination with at least one amphoteric;
        wherein the ratio of anionic and/or nonionic to amphoteric is 100:1 to 1:100
        (b) 0 to 60% by wt. of external phase of a second topically active compound; and
        (c) optional solute.
2. An emulsion according to claim 1 comprising 2 to 90% by wt. $W_1$/O emulsion.
3. An emulsion according to claim 2, comprising 5 to 80% by wt. $W_1$/O emulsion.
4. An emulsion according to claim 1, wherein solute in internal aqueous phase is alkali metal chloride.
5. An emulsion according to claim 1, wherein solute in internal aqueous phase is either sucrose or glucose.
6. An emulsion according to claim 1, wherein oil phase is 1 to 80% of the internal $W_1$/O phase.
7. An emulsion according to claim 1, wherein hydrocarbon is a saturated vegetable based oil.
8. An emulsion according to claim 6, wherein oil is >50% saturated.
9. An emulsion according to claim 7, wherein oil is >85% saturated.
10. An emulsion according to claim 1, wherein the emulsifier (c) is cetyl dimethicone copolyol.
11. An emulsion according to claim 1, wherein the topically active compound (1)(d) is lactic acid.
12. An emulsion according to claim 10, wherein the second topically active compound (2)(b) is lactic acid.
13. An emulsion according to claim 1 wherein topically active compound is nonionic hair styling polymer.
14. An emulsion according to claim 1 wherein topically active compound is polyvinylpyrrolidone.
15. An emulsion according to claim 1, which is stable at a temperature of about 25° C. after 2 weeks.
16. A composition according to claim 12, which is stable after 30 days.

* * * * *